(12) United States Patent
Guirguis

(10) Patent No.: US 6,509,164 B1
(45) Date of Patent: Jan. 21, 2003

(54) LIQUID SPECIMEN CONTAINER AND ATTACHABLE TESTING MODULES

(75) Inventor: Raouf A. Guirguis, Herndon, VA (US)

(73) Assignee: LaMina, Inc., Arlington, VA (US)

( * ) Notice: Subject to any disclaimer, the term of this patent is extended or adjusted under 35 U.S.C. 154(b) by 0 days.

(21) Appl. No.: 09/680,950

(22) Filed: Oct. 10, 2000

Related U.S. Application Data

(62) Division of application No. 09/210,815, filed on Dec. 15, 1998, now Pat. No. 6,210,909, which is a continuation of application No. 08/474,893, filed on Jun. 7, 1995, now Pat. No. 5,849,505, which is a division of application No. 08/340,884, filed on Nov. 15, 1994, now abandoned, which is a continuation of application No. 07/686,934, filed on Apr. 18, 1991, now Pat. No. 5,429,803.

(51) Int. Cl.[7] .............................................. G01N 33/543
(52) U.S. Cl. .............................. 435/7.2; 422/55; 422/58; 422/59; 422/60; 422/101; 422/102; 435/287.1; 435/287.2; 435/287.7; 435/288.1; 435/288.2; 435/288.5; 435/288.6; 435/810; 436/177; 436/178; 436/514; 436/518; 436/536; 436/538; 436/541; 436/810
(58) Field of Search .............................. 422/55, 58, 59, 422/60, 101, 102; 435/7.2, 287.1, 287.2, 287.7, 288.1, 288.2, 288.5, 288.6, 810; 436/177, 178, 514, 518, 536, 538, 541, 810

(56) References Cited

U.S. PATENT DOCUMENTS

| | | | |
|---|---|---|---|
| 3,141,740 A | 7/1964 | Wild | 23/309 |
| 3,647,397 A | 3/1972 | Colmen | 23/309 |
| 4,376,634 A | 3/1983 | Prior et al. | 436/502 |
| 4,458,020 A | 7/1984 | Bohn et al. | 435/296 |
| 4,643,303 A | 2/1987 | Arp et al. | 206/370 |
| 4,786,471 A | 11/1988 | Jones et al. | 422/61 |
| 4,953,561 A | 9/1990 | Guirguis | 128/771 |
| 5,030,555 A * | 7/1991 | Clemmons | 435/5 |
| 5,035,866 A | 7/1991 | Wannlund | 422/102 |
| 5,042,502 A | 8/1991 | Guirguis | 128/771 |
| 5,137,031 A | 8/1992 | Guirguis | 128/771 |
| 5,139,031 A | 8/1992 | Guirguis | 128/771 |
| 5,224,489 A | 7/1993 | Guirguis | 128/771 |

OTHER PUBLICATIONS

Tony Green et al., "Ready–To–Pack Micro–Chromatography Columns", 1990, pp. 1–5.
"Hamilton Chron Prep", Hamilton Company, 1981, pp. 1–7.
"Amicon Introduces Membrane Affinity Chromatography Produce", pp. 6–8.
"Urinalysis", Fisher 88, Fisher Scientific, pp. 1–2.

* cited by examiner

Primary Examiner—Christopher L. Chin
(74) Attorney, Agent, or Firm—Foley & Lardner

(57) ABSTRACT

A biological fluid collection container comprising a cup member, a lid assembly removably mounted to the cup member comprising a housing with a downwardly extending cylindrical skirt, a luer lock with a throughgoing bore extending from one side of the lid housing. A hollow tube extends from the other side of the lid housing adjacent the luer lock and is axially aligned with the throughgoing bore of the luer lock. The hollow tube is provided with a plurality of throughgoing holes leading into its lumen along its surface to provide for a sampling along various liquid level layers of the biological fluid specimen collected in the cup member so that when the biological fluid specimen is removed from the cup member a representative sampling is obtained.

18 Claims, 11 Drawing Sheets

LIQUID SPECIMEN CONTAINER AND ATTACHABLE TESTING MODULES

This application is a division of U.S. Ser. No. 09/210,815, filed Dec. 15, 1998 now U.S. Pat. No. 6,210,909, which is a continuation of Ser. No. 08/474,893, filed Jun. 7, 1995 (now U.S. Pat. No. 5,849,505); which is a division of Ser. No. 08/340,884, filed Nov. 15, 1994, (now abandoned) which is a continuation of 07/686,934, filed Apr. 18, 1991 (now U.S. Pat. No. 5,429,803).

BACKGROUND OF THE INVENTION

1. Field of the Invention

The present invention relates to a container used for collecting urine or other biological liquid specimens and for testing modules which can be removably attached to the container. After the biological liquid has been collected, the lid for the container is replaced and the container sealed by the patient or medical person handling the collection. The present collection container allows for secondary collection of the urine specimen from along different fluid levels of the urine in the container without removing the lid, thereby allowing a specimen to be tested without contamination of the specimen from workers or materials outside the container. This transferring can be done without pouring or pipetting the collecting specimen. It can thus be seen that the present invention is directed to a medical and laboratory biological specimen collecting and testing apparatus. The urine container together with attachable testing modules is used in diagnostic cytology in the area of clinical pathology in which diagnoses are made based upon a microscopic examination of cell and other biological samples taken from a body site. The accuracy of the diagnosis depends both upon adequate patient sampling and culture or slide preparation procedures that result in optimally interpretable specimens.

It is known that prompt processing of urine traditionally has been recommended to ensure accuracy of quantitative culture results, urinalysis and microscopy. This is important in making slides, in that fresh cells stick to the glass slide much better than cells from preserved urine, allowing a smoother cell spread onto the glass body. However, delays in processing and care of both inpatient and outpatient settings and refrigeration is often neglected. One solution to the delay problem is the use of chemical preservation of the urine and this preservation system has been used in the field. The presence of liquid preservative in the urine specimen raises the specific gravity of the specimen to unmeasurable levels and limits the potential usefulness of the urine for various types of traditional quantitative analysis, such as slide microscopy.

A number of urine or other biological liquid specimen containers have been developed allowing liquid biological specimens to be tested without removing the lid of the urine or biological fluid container.

U.S. Pat. No. 2,953,132 discloses a parenteral solution bottle with an inwardly projecting tube and a rubber stopper and an associated dispenser bottle which is adapted to introduce the medication into the parenteral solution bottle.

U.S. Pat. No. 3,066,671 discloses a disposable additive container provided with a cover formed with a shaft guiding sleeve. The shaft guiding sleeve receives an infusion holder and an additive container.

U.S. Pat. No. 3,608,550 discloses a transfer needle assembly for transferring fluid from a fluid source to a fluid collection container. The needle assembly includes a first cannula mounted on a support means which engages the collection container and is adapted to be connected at its forward end to the fluid source and at its rear end to the collection container. A second cannula is mounted on the support means and is adapted to be connected at its forward end to the fluid source and at its rear end to the atmosphere allowing fluid to be transferred from a fluid source to a collection container by atmospheric pressure when the volume within the collection container is sufficiently increased.

U.S. Pat. No. 3,904,482 discloses an apparatus and method for the collection, cultivation and identification of microorganisms obtained from body fluids. The apparatus includes an evacuated tube containing a culture medium, an inert gaseous atmosphere and a vent-cap assembly. The tube containing the culture medium is fitted with a stopper for introduction of body fluid by means of a cannula and, after growth of the organisms, transfer of the cultured medium is completed for subculturing or identification procedures.

U.S. Pat. No. 4,024,857 discloses a micro device for collecting blood from an individual or other blood source into a blood sampler cup. The cup has a removable vented truncated cone shaped top with a capillary tube passing through a well formed in the top proximate to the inside wall of the cup to deliver blood directly from the blood source to the cup.

U.S. Pat. No. 4,116,066 discloses a device for the collection of a liquid, such as urine comprising an open ended urine collection container provided with a hollow cannula attached to its bottom. The cannula is slotted near its base, and serves as the conduit through which liquid may be transferred from the container to an evacuated tube. When the stopper of the evacuated tube is punctured by the cannula, the pressure difference causes liquid deposited in the container to be drawn through the slot into the hollow cannula and into the tube.

Another attempt to solve this problem is seen in U.S. Pat. No. 4,300,404, in which a container is developed having a liquid container with a snap fit lid. The lid is provided with a cannula which extends into the lower end of the container and which projects through the lid at its upper end so as to be able to pierce the stopper of an air-evacuated tubular container. The container is also provided with a depressed bottom to assure the maximum collection of fluids and the lid is provided with a recess to accommodate the air-evacuated tube.

2. Summary of the Invention

The present invention is directed to a liquid collection container having a skirted lid which is adapted to be screwed over the container and a hollow tube connected to the container lid and axially aligned with the bore of an integrally formed luer lock. The tube extends down into the container and is provided with an open end and a series of perforations extending up the length of the tube and communicating with the tube lumen so that different levels of urine or biological fluid maintained in the container can be simultaneously withdrawn from the container by the use of a standard syringe and if desired through a quantitative measuring container for cytology/microbiology applications or through a chromatographic capsule for antigen capture and diagnosis.

It is thus the object of the invention to collect urine or other fluids for use in testing and to protect the fluid from outside contamination and to allow easy transport of the fluid.

In the accompanying drawings, there is shown an illustrative embodiment of the invention from which these and other of the objectives, novel features and advantages will be readily apparent.

DETAILED DESCRIPTION OF THE INVENTION

Figure 1:
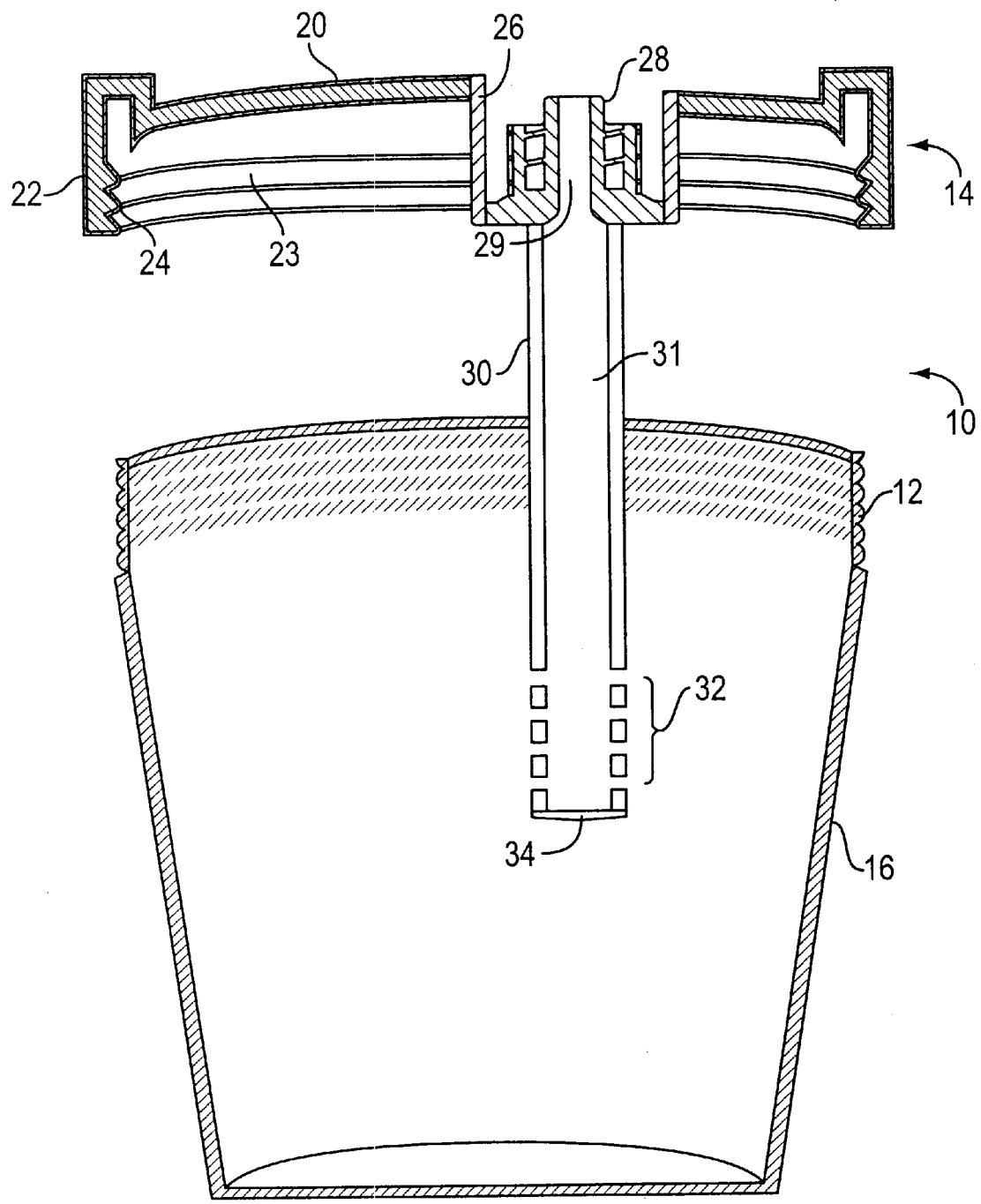
FIG. 1 is an exploded cross-sectional schematic view of the inventive collection container.
Figure 2:
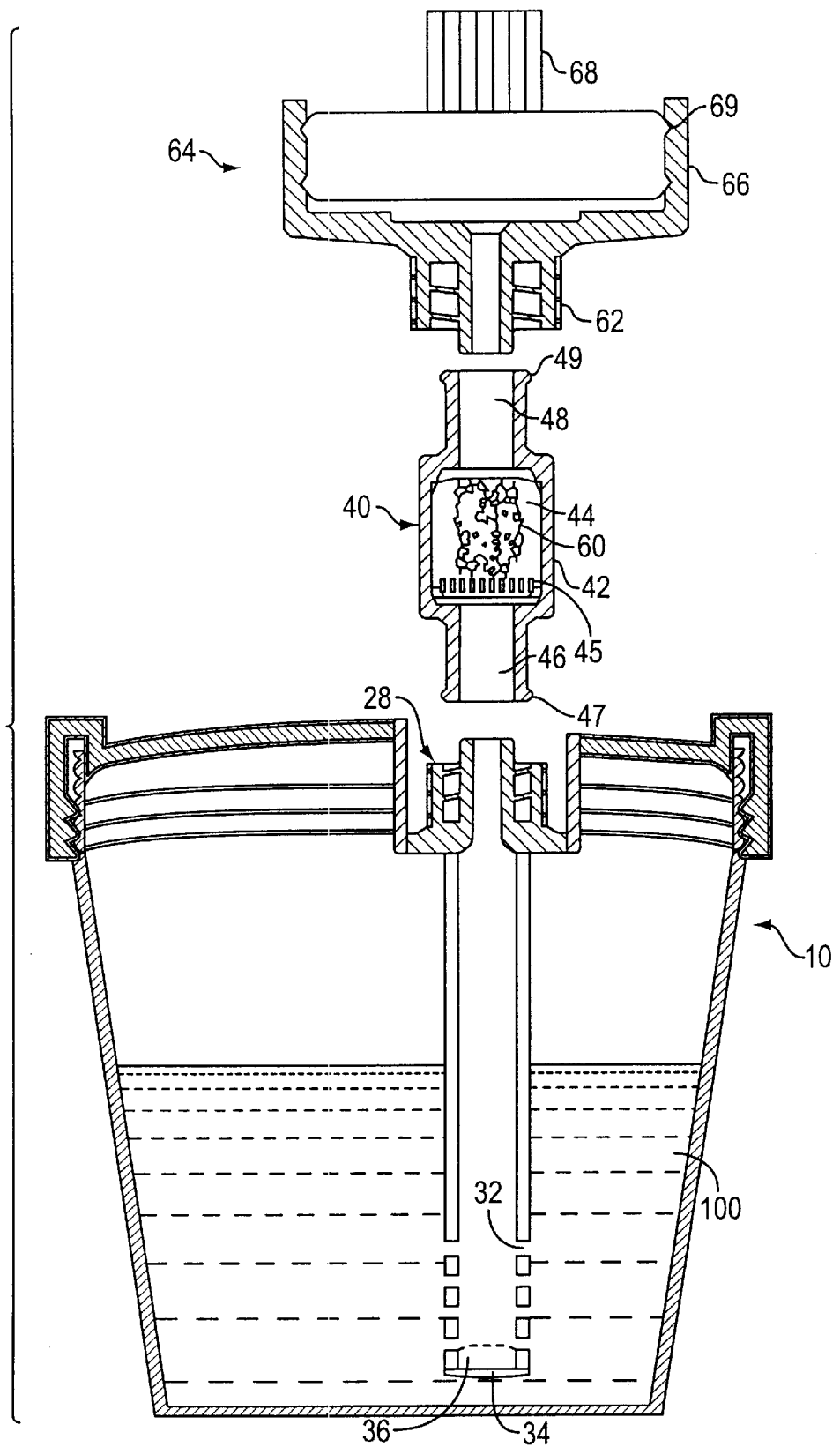
FIG. 2 is a cross-sectional exploded schematic view of a chromatographic capsule for antigen capture being mounted to the luer lock of the collection container of FIG. 1 and operated by a syringe.
Figure 3:
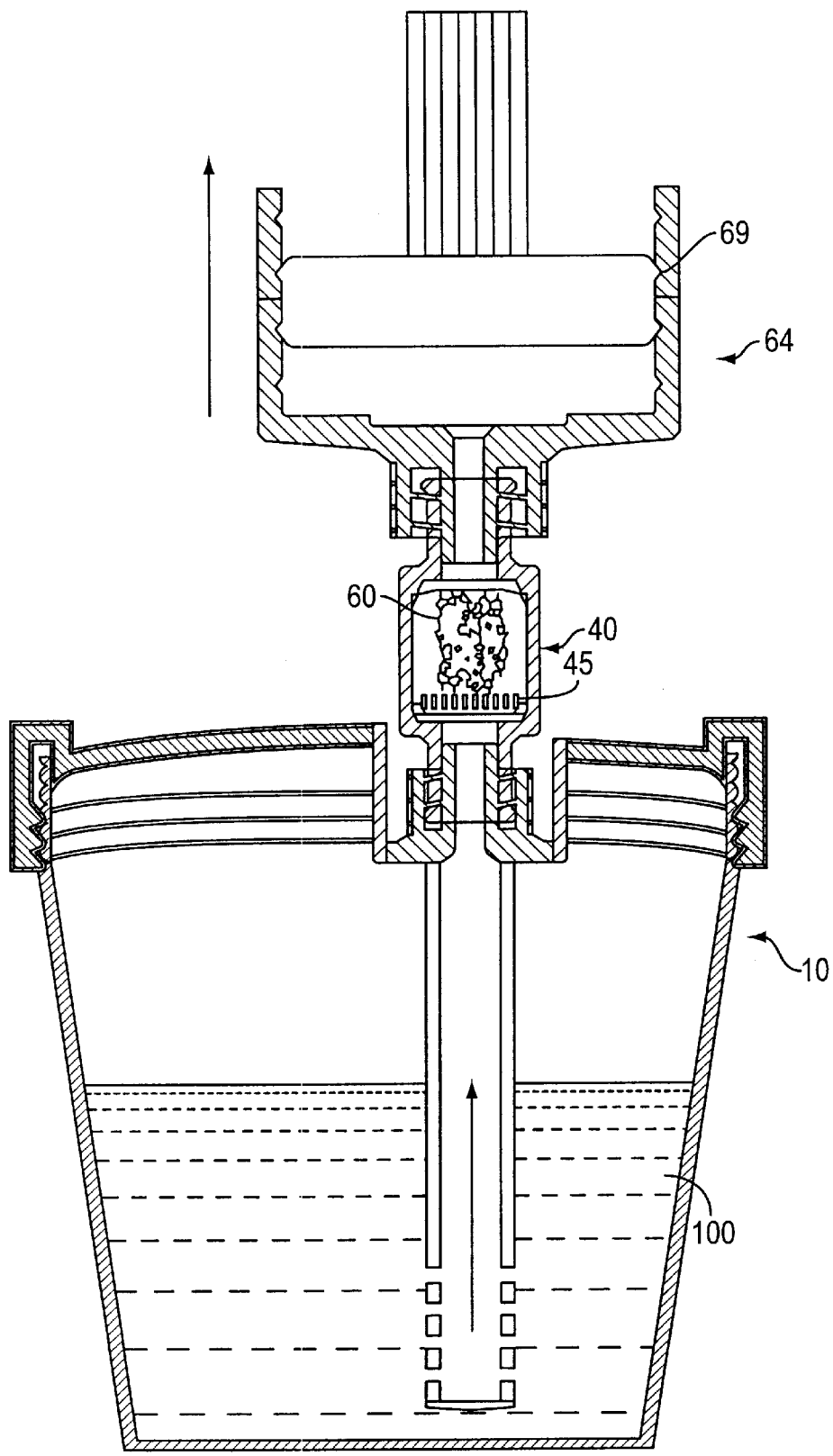
FIG. 3 is a cross-sectional schematic view of the chromatographic capsule for antigen capture connected to the collection container of FIG. 1 with fluid being withdrawn from the container into the syringe barrel for antigen dapture.
Figure 4:
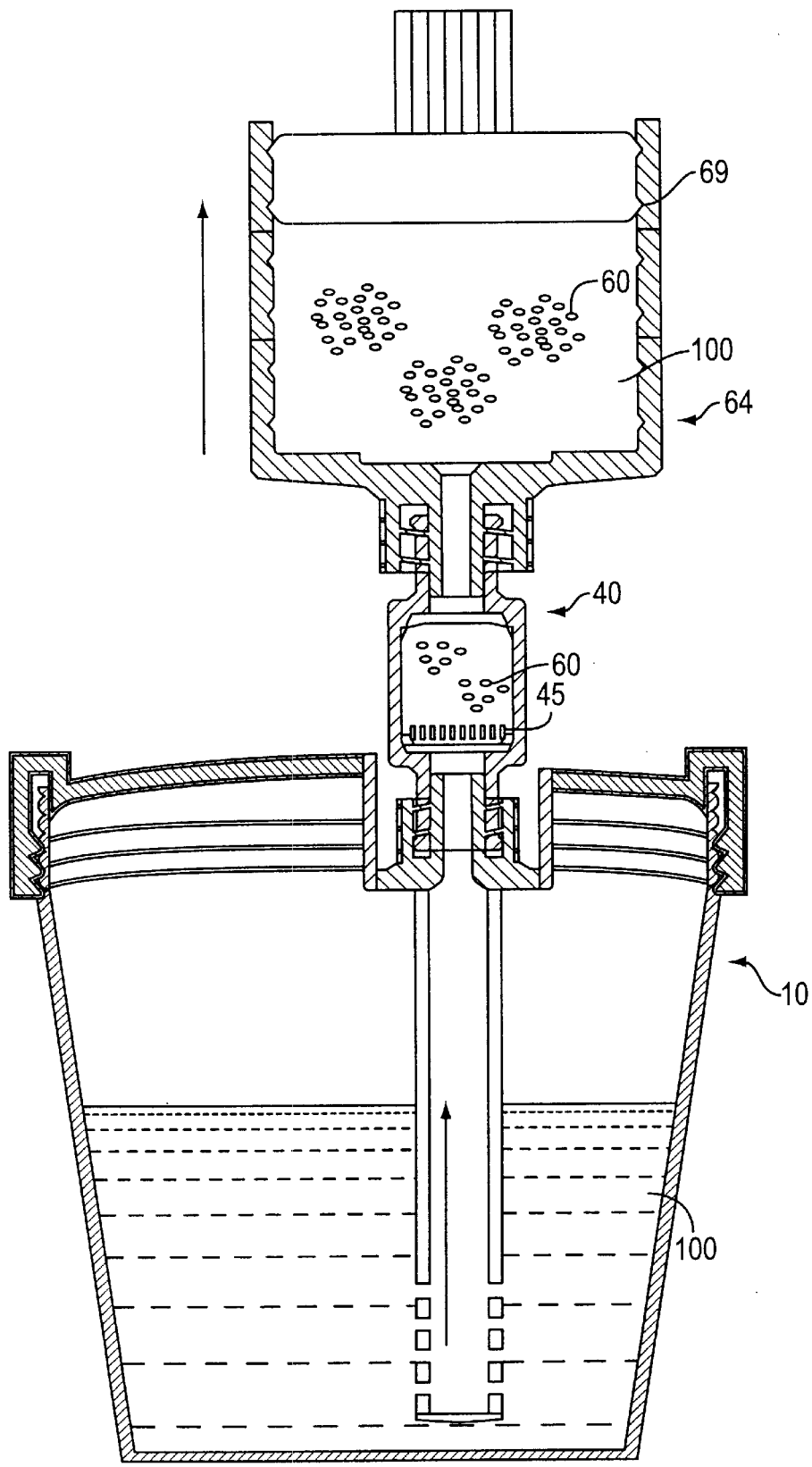
FIG. 4 is a schematic cross-sectional sequential view of the assembly shown in FIG. 3 shown drawing fluid through the chromatographic capsule into the syringe.
Figure 5:
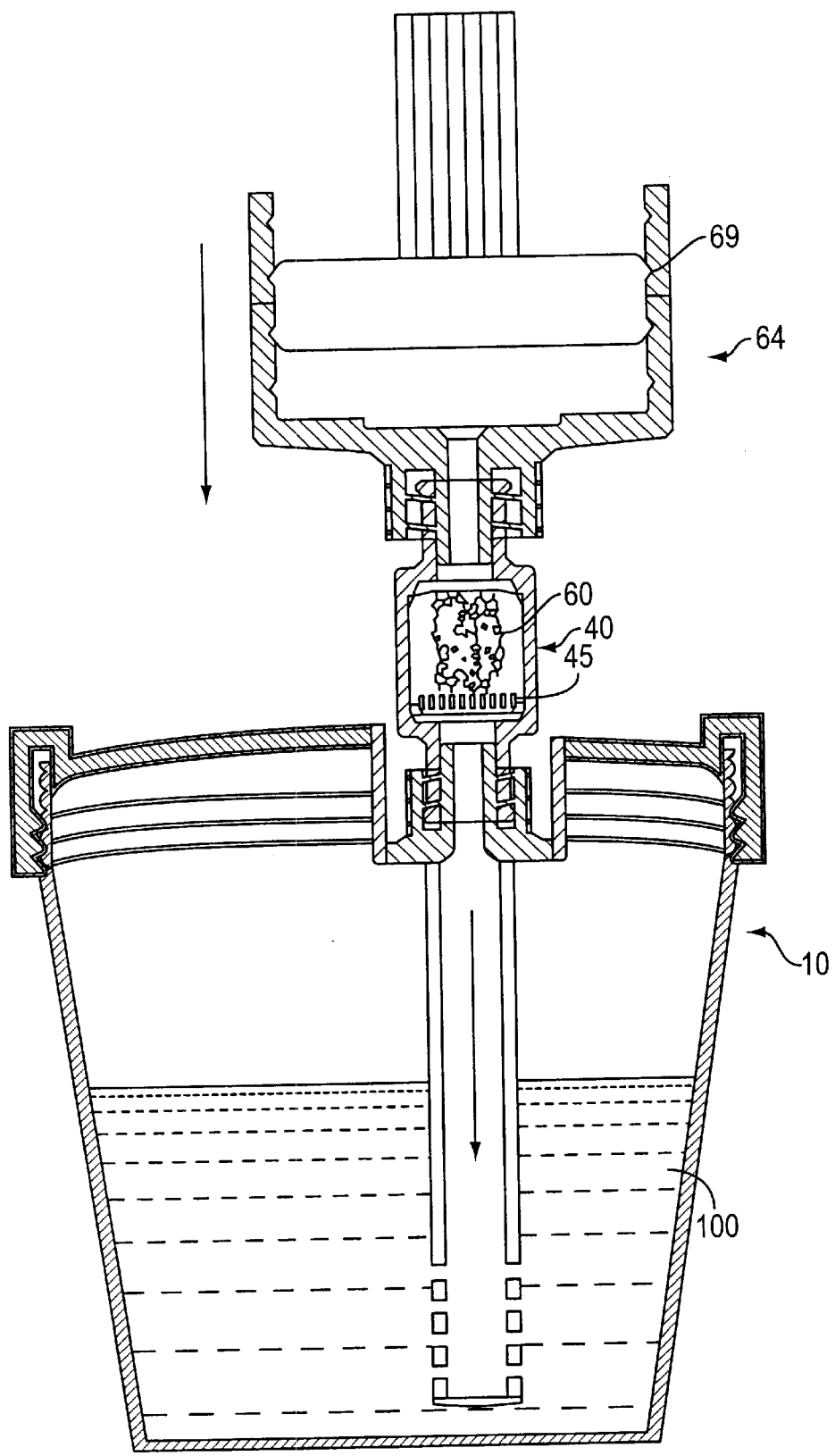
FIG. 5 is a schematic cross-sectional sequential view of the assembly shown in FIG. 4 in which fluid is pumped back into the collection container after antigen capture.

The preferred embodiment and best mode of the invention is shown in FIG. 1 and assembled in FIG. 2 and relates to a urine collection cup 10 in which urine or other biological liquid specimens may be collected. After collection, the patient or supervising medical personnel places a lid 14 on the cup housing 16. The cup housing 16 is provided with an external threaded surface 12. The lid 14 has a housing 20 which is molded with a downwardly directed cylindrical extended skirt or flange 22 which is threaded 24 on its inner surface 23 for threading onto the external threaded surface 12 of cup housing 16. The lid housing 20 defines a well 26 in which is seated an intregally molded threaded luer lock 28. The luer lock 28 is provided with a throughgoing bore 29 leading to a hollow tube 30 which is preferably integrally molded or separately secured to the other side of the lid housing with its lumen 31 being axially aligned with the bore 29 of the luer lock. The tube 30 has a series of perforations 32 extending along its length and an open end 34 which allow different fluid layers to be simultaneously tested when the urine or biological fluid is withdrawn from the cup. If desired, as shown in FIG. 2, a filter 36 of large pore size can be mounted in the open end 34 to provide for filtration of larger urinary sediments in the urine or biological liquid 100.

Figure 6:
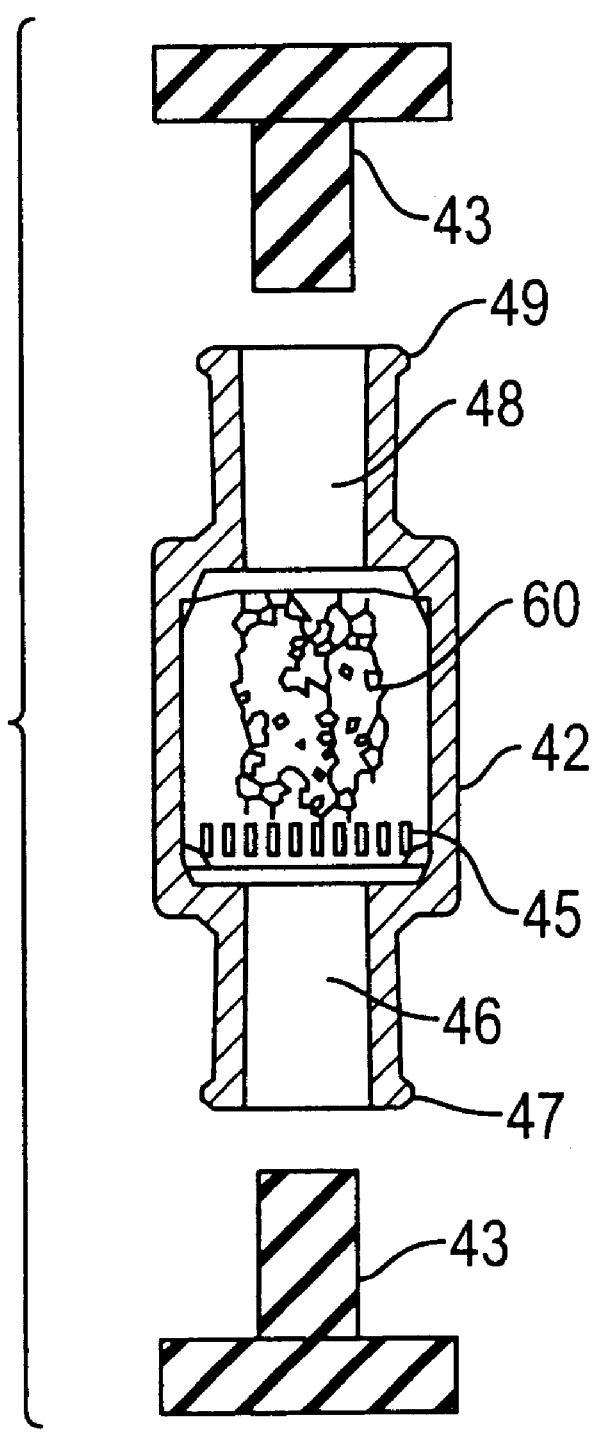
FIG. 6 is a schematic cross-sectional view of the chromatographic capsule used with the urine collection container showing exploded end plugs which can be used to hold the antigen beads in the capsule.

An adapter bead container capsule 40 as seen in FIGS. 2 and 6 is selected to be mounted to the lid luer lock 28. The capsule housing 42 defines a chamber 44 in which is mounted a filter 45 for antigen beads capture. The housing 42 has hollow nipple end members which define an inlet bore 46 which is axially aligned with luer lock bore 29 of the lid and an outlet bore 48 which will be axially aligned with the luer lock bore of syringe 64. End plugs 43 as shown in FIG. 6 seal the capsule 40 after fluid has been passed through the bead chamber to deposit antigen on the beads.

The beads container housing 42 with treatment filter 45 mounted therein preferably has a filter particle size of 5 microns but can range from 1–5 microns or any size which is suitable to allow fluid flow with antigens to pass therethrough but also prevent the passage of beads 60. Each end 47 and 49 of the bead container capsule 40 is fitted with a threaded projection which is adapted to fit onto a luer lock 62 of a 30 cc syringe 64, manufactured by Becton Dickinson & Co. It should be noted that any pump type device could be used in place of the syringe as for example an autovial spunglass filter manufactured by Genex Corporation. The syringe 64 has a barrel 66, piston 68 and piston head 69. While the bead capsule 40 can be used for any body fluid it is primarily designed for use in collecting concentrated urine antigen samples for use in testing for the presence of various kinds of cancer in the body to determine the presence and stage of the cancer.

As shown in FIGS. 2 through 5 the beads container capsule 40 is constructed of polystyrene. The capsule housing 42 defines a urine entrance port 46 and exit port 48. The chamber 44 of the beads container capsule 40 contains a filter 45 and a bed of beads 60 with immobilized antibodies positioned on the syringe side of the filter.

The beads 60 are preferably visible (above 10 micron in diameter) so that their flow into the syringe (see FIG. 4) and back to the capsule 40 (see FIG. 5) can be visually observed to make sure of maximum bead contact with the urine. Antibodies are immobilized (covalently bound) on the beads 60 as is well known in the art and are designed to have binding sites which have a high affinity for the epitopes of the cancer antigens carried in the urine.

It should be noted that the volume of beads 60 is important and the beads should not be greater then the volume of the capsule chamber 44 so that the syringe neck will not become jammed.

The principle of affinity chromatography requires that a successful separation of a biospecific ligand is available and that it can be chemically immobilized to a chromatographic bed material, the matrix. Numbers of methods well known in the art have been used to couple or immobilize antibodies to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

An advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10–100 cm/min).

The resin bead material 60 with matrix and primary ligand (in this case immobilized antibody) having had flow contact with the filtered urine in buffered form from the addition of 10 ml of 200 mM Tris buffer pH 7.8 manufactured by Pharmacia captures through antigen-antibody reaction with or immune reaction the specific ligand component carried by the urine namely, the non complexed antigen. This buffering agent adjusts the urine pH. The buffer solution can be added to the collection container 10 by directly adding it from the syringe 64 prior to withdrawing the urine into the syringe or simply adding it to the collection container 10 from another container. When the specific antigen is present in the urine testing sample 100 the antigen reacts with the antibody to form antigen-antibody complexes. The complexed antigen-antibody carried by beads 60 remains in the housing chamber 44 as is clearly shown in FIG. 5. If there is an absence of the antigen in the specimen sample 100 the antibody will remain unoccupied.

Testing is presently done by using 0.2–0.5 ml aliquots of urine. The present high affinity beads 60 can capture the antigen present in 100 ml or even more of the sample, depending on the frequency of filling and emptying the syringe 64. This will result in 500× fold increase in the amount of antigen being captured by the beads. Preferably the syringe barrel 66 is filled with urine (see FIG. 4) allowing the beads to move freely into the barrel of the syringe for maximum fluid contact and mixing. The syringe is emptied and refilled a number of times for maximum concentration so that 1,000× antigen concentrations from that previously obtainable can be obtained.

The capsule 40 is removed from luer lock 62 of syringe 64 and ports 46 and 48 are closed with plugs 43 as shown in FIG. 6 to provide a capsule filled with concentrated specimen sample that can be shipped. Furthermore the specimen life of the buffered specimen is 6 months or longer under ordinary storage conditions after washing the beads with preservative solution e.g. 0.01% Sodium Agide (Bacteriostatic agents).

Upon receipt of the specimens the container is placed on a syringe containing an eluting buffer which release the antigens from the antibody on the beads providing a concentrated antigen sample for testing purposes.

A cytology/microbiology container 70 is also provided for alternate use with the collection container. Both the cytology container 10 and antigen beads container capsule 40 are each adapted to be removably mounted to a syringe 64 which is of standard construction.

Figure 7:
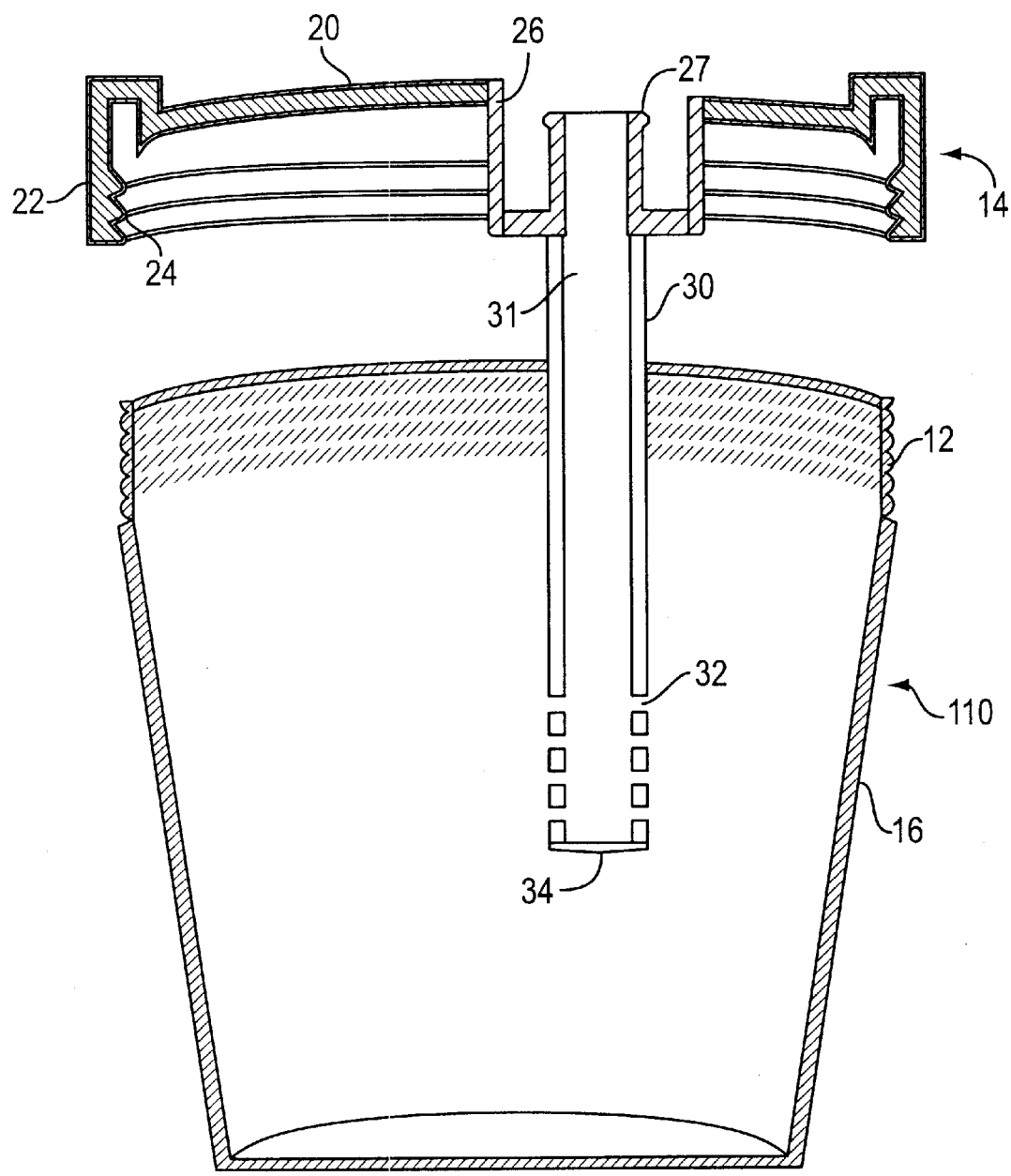
FIG. 7 is an alternate embodiment of the collection container using a female luer lock modification.
Figure 8:
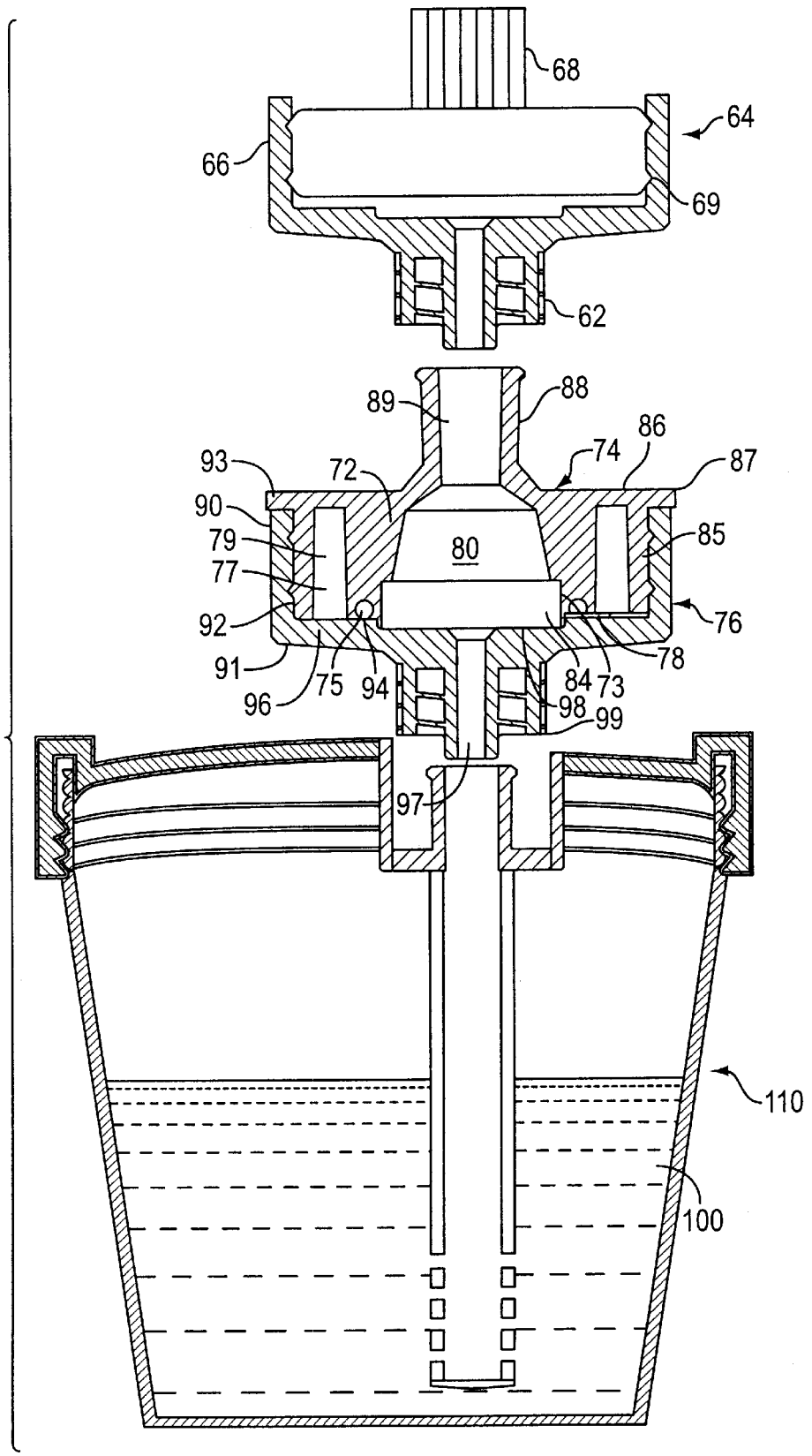
FIG. 8 is a schematic exploded cross sectional view of a cytology/microbiology container being attached to the female luer lock embodiment of FIG. 7.
Figure 9:
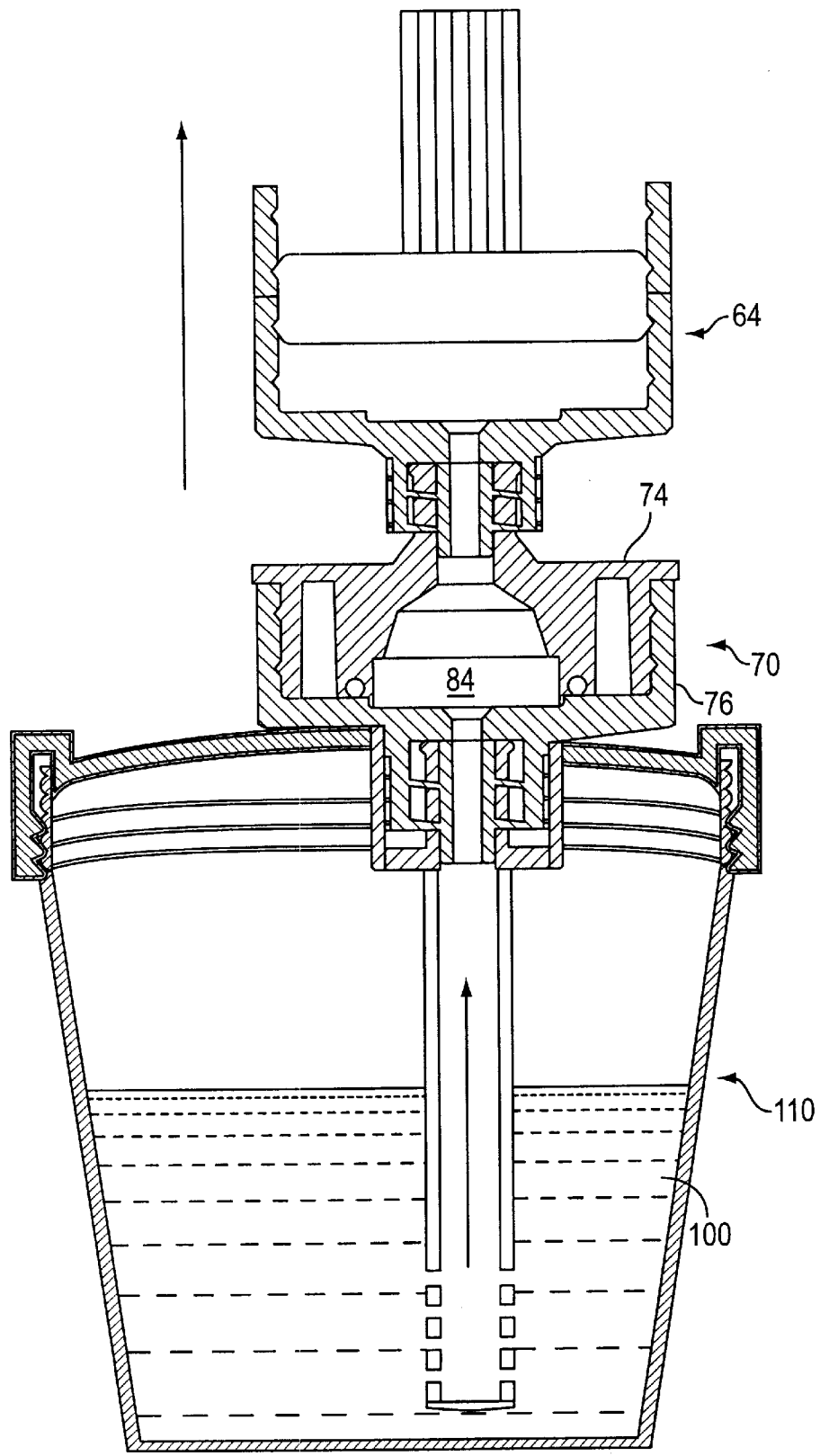
FIG. 9 is a schematic cross sectional sequential view of a cytology/microbiology container attached to the female luer lock embodiment and a syringe.

The cytology/microbiology container 70 as more clearly shown in FIGS. 8–11 is alternately mounted to syringe luer lock 62 and the female luer lock 27 of collection cup 110 shown in FIG. 7. Each cytology/microbiology container is easily opened and is constructed with a simple two-piece construction comprising a male filter membrane carrying member 74 and a female connector member 76 screwed onto the male member. The male filter membrane member 74 is provided with an outer cylindrical wall 85 having a threaded external surface 71, a base 86 which extends past the cylindrical wall 85 to form a lip 87, and a male nipple 88 which extends outward from the base in an opposite direction from wall 85. The nipple 88 is provided with an end flange which is adapted to be threaded into the threaded luer lock 62 of the syringe 64 and defines a throughgoing bore 89 which leads into chamber 80 defined by an inner inclined wall 72 of the male member. The inner wall 72 has a cylindrical exterior surface 79 and is spaced from the inner surface of outer wall 85 to define a channel 77. An annular step or membrane seat 73 is cut into the inner surface of wall 72 to hold filter membrane 84. An annular channel 75 is cut into the surface of stepped end 78 of the inner wall 72 allowing the stepped end to fit over locking prongs 94 extending from the female member thus holding the male and female members in a sealed relationship while providing a safety stop for the filter membrane 84.

The female connector member 76 has an outer cylindrical housing 90 with a base 91. The housing is threaded on its inner surface 92 for engagement with the threaded external surface 71 of wall 85. The planar end wall 93 of housing 90 abuts against the outwardly extending flange or lip 87 when the male and female members are screwed together. The female connector base inner surface, which in combination with the inner wall surface of housing 90 defines the interior configuration of the female member, is concentrically stepped so that the outer step 96 abuts against the end of walls 85 and 72 and an inner step 98 abuts against filter membrane 84 and the distal stepped portion 79 of stepped end 78. The base 91 is provided with a threaded luer lock 99 on its exterior surface and defines a throughgoing bore 97 with a frustro conical proximal end which leads to membrane 84 and chamber 80. As previously noted, nipple 88 of the cytology/microbiology container is fitted with a threaded projection which is adapted to fit onto the luer lock 62 of a 30 cc syringe 64, manufactured by Becton Dickinson & Co. It should be noted that any pump type device could be used in place of the syringe 64 as for example an autovial spunglass filter manufactured by Genex Corporation. The syringe 64 has a barrel 66 with associated luer lock 62, piston 68 and piston head 69. While the cytology/microbiology container 70 can be used for any body fluid it is primarily designed for use with concentrated dialysis fluid and urine and for collecting associated sediments and/or bacteria for use in testing for various kinds of disease.

Figure 10:
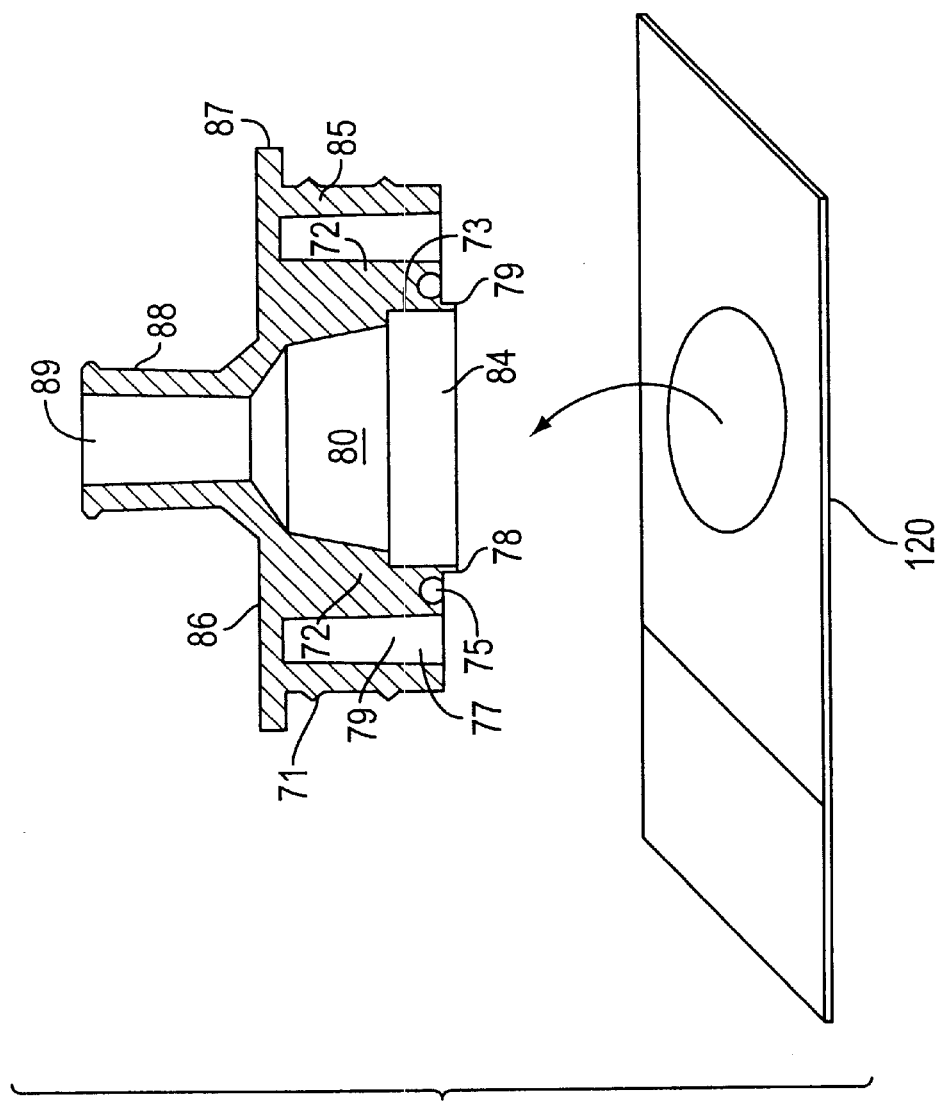
FIG. 10 is a cross-sectional view of a removed male member from the cytology container being placed on the side for cytology examination.
Figure 11:
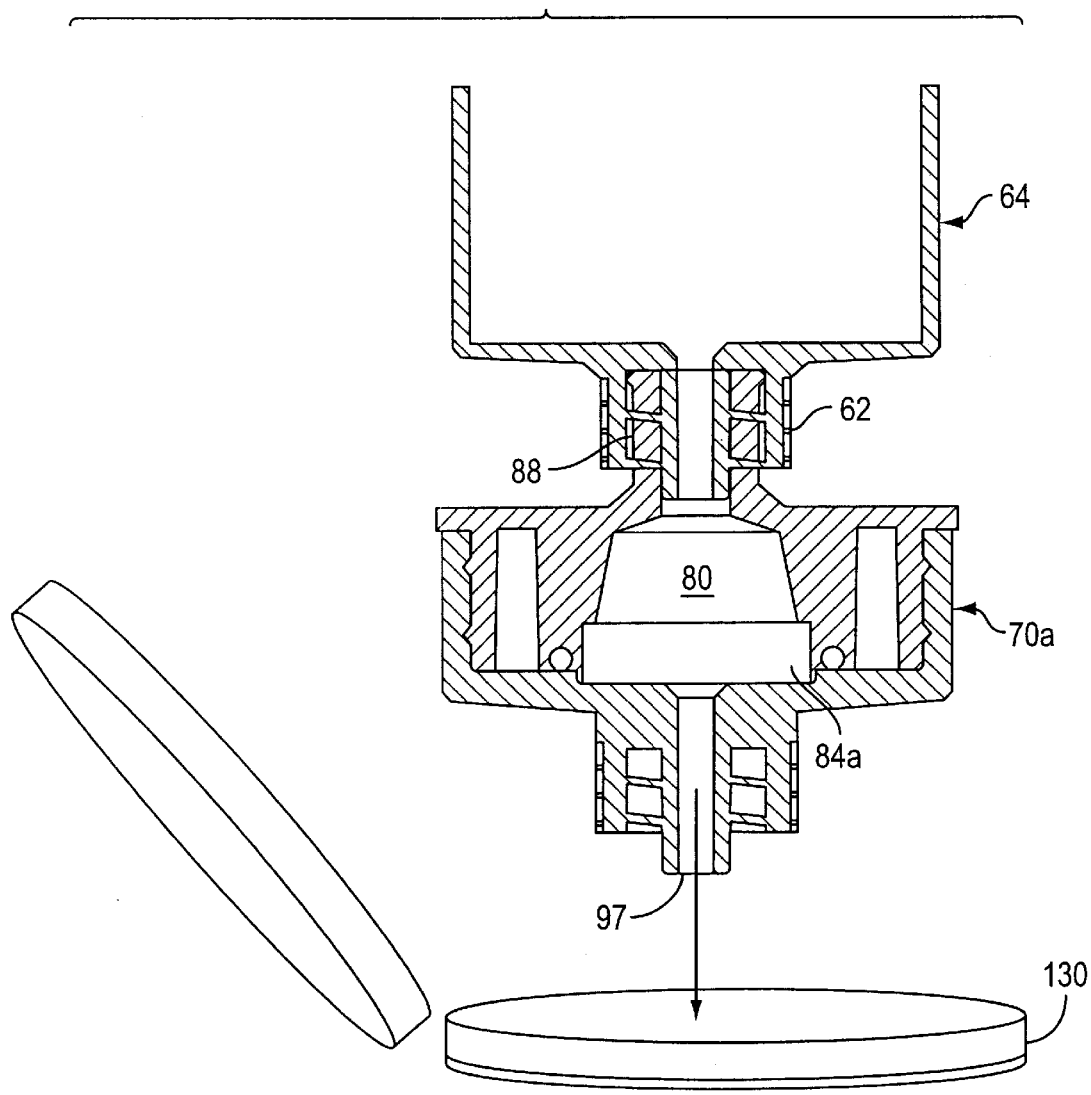
FIG. 11 is a cross-sectional view of a microbiology container with collection container removed, eluting a bacteriological sample into a microbiological culture tray.

The male member 74 of the cytology/microbiology container 70 can contain a nitrocellulose membrane filter 84a with a filter size of 13 mm diameter and a porosity of approximately 0.45 microns for bacteria entrapment as shown in FIG. 11 or in the case of cell cytology, a polycarbonate filter 84, as shown in FIG. 10. The polycarbonate filter 84 has a five-micron pore size to trap the polymorphnuclear leukocytes or even lymphocytes which are seven and one half microns in size.

It should be noted that various composition filters can be used and interchanged. One membrane filter that can be used for fluid screening is LEUCOSORB , a leucocyte retention medium manufactured by Pall BioSupport Division of Pall Corporation. Other membranes manufactured and sold by the Pall Corporation are BIODYNE A, an unmodified nylon with surface chemistry 50% amine and 50% carboxyl group with an isoelectric point of pH 6.5; BIODYNE B, a surface-modified nylon with surface chemistry characterized by a high density of strong cationic quarternary groups (the zeta potential is positive to pH>10); BIODYNE C, a surface-modified nylon with surface chemistry characterized by a high density of anionic carboxyl groups (the zeta potential is negative to pH>3; and LOPRODYNE, a low protein binding nylon 66 membrane with a tightly controlled microporous structure with high voids volume for rapid, efficient throughput of liquids and absolute retention of microparticles designed for cell separation and bacterial cell immunoassays. Fifty milliliters of dialysate will be pulled from container 10 through the desired filter membrane 84 or 84a depending upon the analysis into syringes 64. After the requisite amount of dialysate has been passed through the filter membrane, the cytology/microbiology container 70 and associated filter membrane is removed. The polycarbonate membrane 84 is placed on a glass slide 120 as shown in FIG. 10 and stained with a modified Wrights stain for cytologic determination.

Thus, the method of transferring cells to a slide is that of membrane filtration (filtration of fluid specimens through membrane filters to increase cell recovery). This particular technique provides the critical feature that the cells are evenly deposited over the slide with minimal overlap as this will allow clear observation and optimal diagnostic accuracy.

It should be noted that the process of transferring or collecting cells onto a slide or membrane is largely affected by preserving or fixing the cytology specimen in the body fluid, secretions or smears.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives prior to transferring cells onto the slide or membrane for staining or examination.

It has been found by the present inventor that the recovery (yield) as well as the quality of the cytology preparations from fresh body fluid specimens is superior when compared to routine cytology preparations that were prepared when the same samples were preserved. This is probably due to the fact that fresh cells stick better to glass and/or membranes than those preserved in alcohol or other preservatives.

The inventive apparatus also allows for isolation and collection of fresh cells and/or microorganisms from the body fluids to perform DNA probing and chromosomal analysis once the cells are hemolysed by the proper buffer.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatin patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eye strain.

Since cellular detail is dependent on fixation, it is extremely important that cells be fixed immediately after being deposited on the slide. Too long a delay between preparation and fixation exposes the cells to air drying, which is detrimental to the cellular structure. Moreover, air drying artifact can adversely affect the subsequent staining results. (An exception is when the cells are stained with Wright-Giemsa, where air drying is used as the fixation step.)

New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The effectiveness of transferring the cells from the filter to the slide has proved to be very high without differential cell loss. (Microscopic examination showed that the cell distribution was the same on the slide as on the filter.)

This procedure has many advantages for conventional cytology. The cells are in a predetermined area allowing for significant timesaving when screening the slide. Such problems as cells lying outside the coverslip or on the frosted end are eliminated. Because cells are lying in a single layer, they are almost always in a one focal plane when using a 10× objective—the objective most often used for the lower power screening of a slide. Even wit a 40× objective, most cells are in focus. This eliminates frequent refocusing and saves time.

The minimal cell overlap achieved in this process ensures that all cells and cell groups can easily be examined with little chance for diagnostic cells to be obscured by clumps of overlapping cells or debris. Moreover, because the process takes place in the cytology laboratory, slide preparation and fixation are controlled by laboratory personnel and quality assurance is easily implemented.

Multiple specimens can be made from a single patient sample. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

In bacteria testing the filter 84a while shown in FIG. 11 to be eluted and cultured in a standard petri dish 130 is preferably used for culturing with a Qualture device not shown but readily obtainable to determine the presence of specific bacteria colonies. The Qualture device is a plastic capsule containing a filter membrane and four nutrient pads of dehydrated, selective media.

The Qualture technique is more sensitive than the agar plate method and more rapid in determining a presumptive diagnosis. The device screens, isolates and presumptively diagnoses bacterial isolates in one step most often in 4–6 hours. Tests have demonstrated that recovery from fifty milliliters of fluid is excellent and sensitive.

Thus it can be seen that the collection cup 10, syringe 64, antigen capture capsule 40 and cytology/microbiology container can be provided in kit form for easy use by the testing person in the desired mix and match combination.

In the foregoing description, the invention has been described with reference to a particular preferred embodiment, although it is to be understood that specific details shown are merely illustrative, and the invention may be carried out in other ways without departing from the true spirit and scope of the following claims.

What is claimed is:

1. An apparatus comprising a plurality of stacked specimen collection containers in fluid communication with one another, each container having an inlet and an outlet and defining at least one fluid flow path through the container, at least one container having chromatographic bed material for capturing particulate matter and cells.

2. The apparatus of claim 1 further comprising at least one specimen collection container having a membrane which captures cells.

3. The apparatus of claim 1 wherein a container having chromatographic bed material for capturing particulate matter includes chromatographic bed material for determining the presence of a specific analyte.

4. The apparatus of claim 1 wherein a container having chromatographic bed material for capturing particulate matter includes chromatographic bed material for determining the presence of multiple analytes.

5. The apparatus of claim 1 further comprising a container housing having a second inlet and a second outlet and having a filter membrane for capturing cells disposed between the second inlet and the second outlet.

6. The apparatus of claim 5 wherein the second inlet communicates with a specimen cup, and the second outlet communicates with a pump.

7. The apparatus of claim 5 wherein the membrane for capturing cells captures cells in a single layer.

8. The apparatus of claim 1 wherein the container having chromatographic bed material includes a membrane which allows the bed material to pass freely out of the outlet.

9. The apparatus of claim 8 wherein the container having chromatographic bed material includes a membrane which prevents the chromatographic bed material from passing into the inlet.

10. The apparatus of claim 1 wherein the specimen collection containers are removable from the apparatus.

11. An apparatus comprising:

a first housing having a first inlet and a first outlet and having a filter membrane for capturing cells disposed between the first inlet and the first outlet; and a second housing having a second inlet and a second outlet and having a chromatography element disposed between the second inlet and the second outlet, wherein the first and second housings are alternately connectable to a specimen cup.

12. The apparatus of claim 11 wherein the first inlet can communicate with a specimen cup.

13. The apparatus of claim 12 wherein the specimen cup includes a lid having a tube extending into the container, said tube having at least two perforations extending along its length.

14. The apparatus of claim 11 wherein the first outlet can communicate with a pump.

15. The apparatus of claim 11 wherein the second inlet can communicate with a specimen cup.

16. The apparatus of claim 11 wherein the second outlet can communicate with a pump.

17. An apparatus comprising:

a first housing having a first inlet and a first outlet and having a filter membrane for capturing cells disposed between the first inlet and the first outlet;

a second housing having a second inlet and a second outlet and having chromatographic bed material disposed between the second inlet and the second outlet; and a specimen container having a lid suitable for fluid communication with the first inlet or the second inlet, said lid having a tube extending into the container, said tube having at least two perforations extending along its length.

18. A kit comprising at least two selected from the group consisting of a chromatography housing, an assay housing, and a cytology housing, wherein said at least two housings are alternately connectable to a specimen cup.

* * * * *